United States Patent [19]

Benjamin

[11] 4,114,612

[45] Sep. 19, 1978

[54] TENSION RELIEVING DEVICE

[76] Inventor: Ben E. Benjamin, 910 W. End Ave. at 105th St., Apt. 15F, New York, N.Y. 10025

[21] Appl. No.: 735,370

[22] Filed: Oct. 26, 1976

[51] Int. Cl.² ............................................... A61F 5/01
[52] U.S. Cl. ................................. 128/76 R; 5/327 B; 5/337; 128/69
[58] Field of Search ................... 128/76 R, 78, 68, 69; 5/327 R, 327 B, 337

[56] References Cited

U.S. PATENT DOCUMENTS

| 1,151,894 | 8/1915 | Meinecke | 5/327 X |
| 3,258,790 | 7/1966 | Maru | 128/68 X |

FOREIGN PATENT DOCUMENTS

| 1,241,643 | 8/1960 | France | 5/327 B |
| 542,823 | 5/1956 | Italy | 5/327 R |

Primary Examiner—Robert W. Michell
Assistant Examiner—Michael H. Thaler
Attorney, Agent, or Firm—Caesar, Rivise, Bernstein & Cohen, Ltd.

[57] ABSTRACT

A device for releasing muscular tension of the head-neck region of the user. The device comprises three elongated members each having a free edge, each edge projects at a 120° angle to the immediately adjacent edge. The cross section of each edge is arcuate, with the first edge being of a first relatively small diameter, the second edge being of a second even smaller diameter and the third edge being of a third still smaller diameter. The device is arranged to be disposed upon a surface upon which the user lies, with two free edges disposed on said surface thereby forming a base and with the remaining edge projecting upward and exposed to support the occipital area of the user as the user lies on said surface to thereby apply muscle tension-relieving pressure to said area.

5 Claims, 4 Drawing Figures

TENSION RELIEVING DEVICE

This invention relates generally to muscular therapy devices and more particularly to devices for relieving muscular tension.

As is known, tension is created when a muscle contracts. It is normal for muscles to contract and release. It is this very pulsation of tension and relaxation which makes one's heart beat, enables one to move, sit, walk, run and even breathe. Without some tension in one's muscles a person would collapse. Accordingly, a certain amount of tension is desirable. But tension is also destructive when muscles contract and stay contracted, unable to relax. It is this excess tension which should be relieved. Failure to relieve such excess tension produces pain, renders the body less resilient and therefore more prone to injury while using up energy as well.

Symptoms of head and neck tension are numerous. Among the commonly experienced symptoms of such tension are headaches, frown lines, the grinding of teeth during sleep, stiff necks, shoulder pain, difficulty in turning one's head from side to side, difficulty in lying prone with the head turned to the side, insomnia, etc.

The device of the instant invention is arranged to effect the release of excess tension in the head-neck area. To that end, the device works by applying pressure to muscle(s) beyond the point of tolerance. Each muscle can tolerate only a certain amount of tension. Accordingly, if one temporarily increases tension in the muscle by applying pressure beyond the point of tolerance, the muscle will release some of its tension. If this is done over a period of time the muscle can relax.

When a muscle contracts, it pulls away from its attachment to the bone; therefore the greatest amount of tension is frequently near the attachment of the muscle to the bone. Pressing very firmly at the point of attachment often releases tension. Since there are many very small muscular attachments at the occiput, this area can be a focal point for tension in the head and neck.

Applying pressure with the device of the instant invention at the occiput releases head tension and allows the neck and shoulder muscles to let go as well.

Tension occurs in the body in muscle groups. One muscle usually does not contract alone, so that when there is tension seemingly in one muscle only, a complex of muscles is actually involved in the contraction. Likewise, when a person has tension in the back of his head, it usually indicates that there is tension in many other muscles in the head. The device of the instant invention serves to relax the neck muscles in the occipital region.

Accordingly, it is a general object of the instant invention to provide a device for effecting muscular tension release in the head-neck area.

It is a further object of this invention to provide a relatively simple and inexpensive device for effecting muscular tension release in the head-neck area of the user.

It is still a further object of this invention to provide a device which is adapted to provide various amounts of pressure to the muscles at the occipital area to enable the user to tailor the action of the device to his own physical condition.

These and other objects of the instant invention are achieved by providing a device for relieving muscular tension in the head-neck area of the user. The device comprises support means and first pressure applying means projecting from the support means. The pressure applying means has an elongated free edge. The cross section of the edge is arcuate and of a first relatively small diameter. The device is adapted to be supported in position such that the free edge is in contact with the occipital area of the user to apply concentrated pressure to the muscles at said contact area to effect the relaxation of tension from said muscles.

Other objects and many of the attendant advantages of the instant invention will be readily appreciated as the same becomes better understood by reference to the following detailed description when considered in connection with the accompanying drawing wherein.

Figure 1:
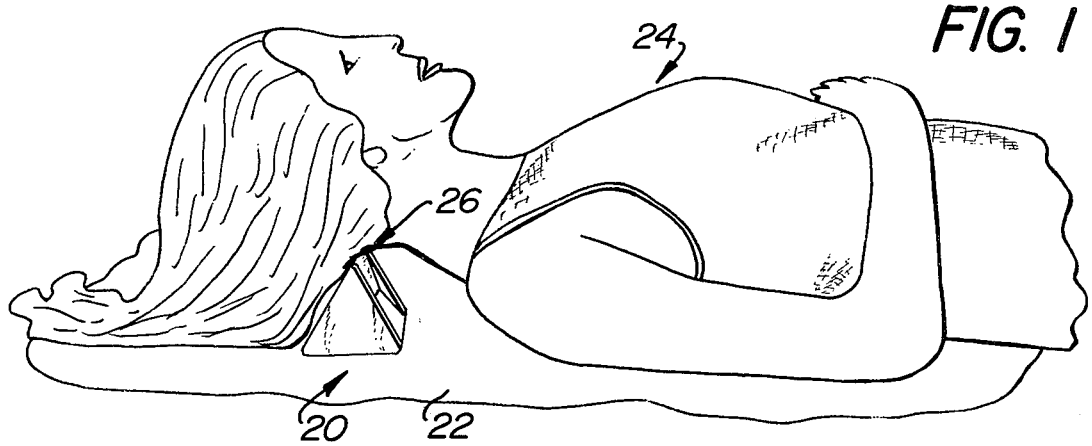
FIG. 1 is a perspective view of the device of the instant invention in use by a person reclining on a horizontal surface.

Referring now to the various figures of the drawing wherein like reference characters refer to like parts, there is shown in FIG. 1 a tension relieving device 20 in accordance with the instant invention and shown in a typical manner in which the device is used.

As will be described in detail later, the device 20 is adapted for disposition on a flat surface 22, such as a floor, etc., and upon which a person 24 using the device reclines. The device is located under the head of the user such that a portion of it, to be described in detail later, makes contact with the occipital area 26 of the user.

Figure 2:
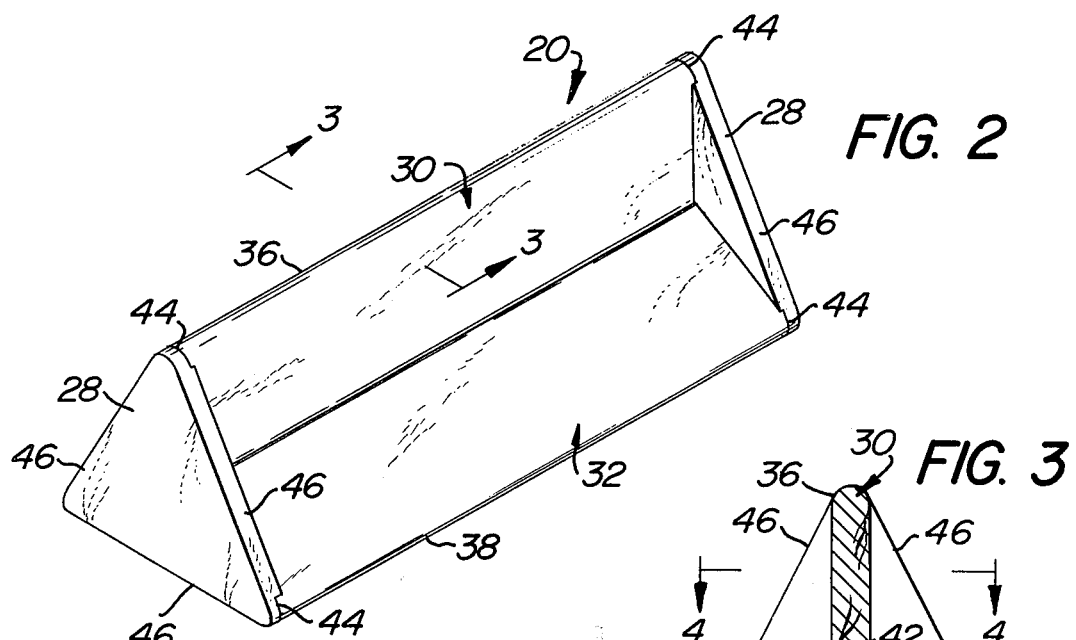
FIG. 2 is an enlarged perspective view of the device of the instant invention.
Figure 3:
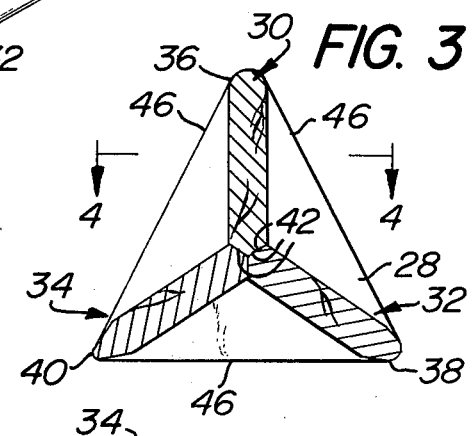
FIG. 3 is a sectional view taken along line 3—3 of FIG. 2.
Figure 4:
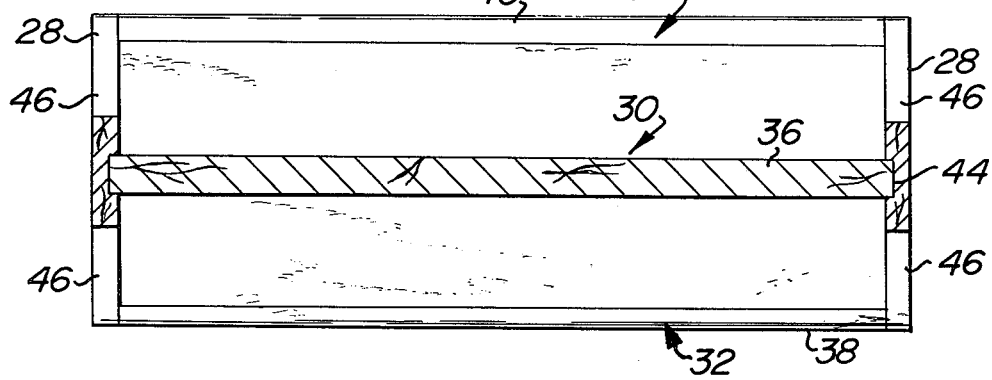
FIG. 4 is a sectional view taken along line 4—4 of FIG. 3.

As can be seen in FIGS. 2–4, the device 20 basically comprises a pair of opposed end pieces or members 28 and three elongated pressure applying members, 30, 32 and 34, extending between the end pieces 28. Each of the pressure applying members is a generally planer piece having an arcuate free edge. To that end, member 30 includes arcuate free edge 36 (FIG. 3), member 32 includes arcuate free edge 38 (FIG. 3) and member 34 includes arcuate free edge 40 (FIG. 3).

As can be seen in FIG. 3, the members 30, 32 and 34 each extend in different radial directions, with the free edges of each member equidistantly spaced, whereupon each free edge extends in a direction at an angle of 120° to that of the immediately adjacent free edge. Each planar member also includes a tapered internal edge 42, with the internal edges 42 of each member abutting one another at the apex of members 30, 32 and 34.

The pressure applying members 30, 32 and 34 are held in the orientation shown in FIG. 3 via the end pieces 28. To that end, each of the end pieces include a respective groove 44 (FIGS. 2 and 4) in which the side edge of an associated pressure applying member is seated and secured, such as by the use of adhesive.

As can be seen in FIGS. 2 and 3, each of the side pieces 28 is in the form of an equilateral triangle. Each side of the equilateral triangle is denoted by the reference numeral 46 and is coextensive in length with the distance between the free ends of immediately adjacent pressure applying members.

As should be appreciated, the sides 46 of the end pieces 28 as well as the free edges of those pressure applying members bridged by said side 46 serve as a base for the device 20 when disposed on surface 22. With the base of device 20 disposed on surface 22, as described above, the free edge of the pressure applying member not forming any portion of the base extends upward from surface 22 and is thereby exposed and available for contact with the occipital area of the user's body to effect the tension relief of the muscles at said area.

It must be pointed out at this juncture that while the device 20 shown in FIGS. 2, 3 and 4 is constructed of various separate pieces, joined together, it is clear that this invention contemplates the construction of device 20 as an integral unit, such as by molding, casting, etc.

In accordance with one aspect of the instant invention each of the free edges of all of the pressure applying members, 30, 32 and 34, are of circularly arcuate shape. However, in the preferred embodiment of the instant invention each edge is of a different diameter.

To that end, as can be seen in FIG. 3, free edge 36 of pressure applying member 30 is of a larger diameter than free edge 38 of pressure applying member 32. Similarly, free edge 38 of pressure applying member 32 is of a larger diameter than free edge 40 of pressure applying member 34.

Free edge 36, being of the largest diameter serves to somewhat spread out the applied pressure, thereby resulting in the least concentrated pressure applied to the occipital area. Arcuate free edge 38, being of a smaller diameter than arcuate free edge 36, serves to apply a more concentrated pressure to the occipital area when pressure applying member 32 is used. Needless to say when free edge 40 of pressure applying member 34 is utilized, the most concentrated pressure is provided to the occipital area.

As will be seen hereinafter, when device 20 is first utilized it is suggested that pressure applying member 30 and its concomitant arcuate edge 36 be used first, followed by the use of pressure applying member 32 and its concomitant arcuate edge 38 and finally ending with the use of pressure applying member 34 and its concomitant arcuate edge 40.

Notwithstanding the relationship between the diameter of each of the edges, all of the edges are of a relatively small diameter so as to apply a relatively concentrated force at the occipital area of the user. Too diffuse a force may not be effective for the release of excess tension from the muscles in the occipital area.

As can be seen in FIG. 3, the diameter of arcuate free edge 36 is approximately twice that of arcuate free edge 38, which in turn is approximately twice that of arcuate free edge 40.

It has been found that a device 20 having an arcuate edge 36 of 7/32 inch (5.56 mm), an arcuate edge 38 of 3/32 inch (2.38 mm) and an arcuate edge 40 of 1/32 inch (0.79 mm) diameter is particularly effective. It should be noted at this juncture that such dimensions are merely exemplary of one device 20 which has proved effective. Other dimensions are, of course, contemplated.

Use of the device 20 to effect the relief of muscular tension in the head-neck region is as follows: the user 24 lies on his or her back on a firm support, such as a firm bed or floor 22. The device 20 is then placed on the surface 22 directly under the back of the user's head with the largest diameter arcuate edge, namely, 36, pointed upward as shown in FIGS. 2 and 3. The device should be positioned such that edge 36 is at the occiput area. The occipital region of the head is where the base of the skull meets the neck as indicated generally by arrow 26 and includes an upper occipital line and slight therebelow a lower occipital line. The edge 36 is first used to support the upper occipital line of the user.

When using the device the user should try to relax the muscles of the neck. If the edge 36 proves too sharp or painful a cushioning implement, such as a folded towel, etc., can be placed over the edge. This will lessen the intensity of edge 36. The towel can later be discarded.

With the occiput now disposed on the edge 36 the user then rolls his or her head very slowly, first to one side then to the other. If during such action a sore point is discovered the user then leaves his or her head in that position for ten or fifteen seconds. The user continues to roll his or her head, finding all the painful points. If the applied pressure proves too intense to stop at the painful points the user may continue to roll his or her head over such points. Continual slow, rolling motion is often easier to tolerate at first. After the edge 36 is used on the lower occipital line its use is repeated on the upper occipital line.

Later, when the use of curved edge 36 of pressure applying member 30 does not hurt on either the upper occipital line or the lower occipital line, the device is then used with the intermediate diameter arcuate edge 38. To that end, the device is positioned such that members 30 and 34 point downward forming, with the sides 46 of the end pieces bridging such members, a base for the device and with the pressure applying member 32 and its concomitant intermediate curved edge 38 pointing upward. The process as described heretofore is then repeated with edge 38. When edge 38 no longer causes pain on both occipital lines the device is then utilized with its smallest diameter free edge 40. The process of using edge 40 is the same as with regard to edges 36 and 38.

As a generaly matter when using any of the edges 36, 38 and 40 of device 20 one should try to keep one's jaw loose and slightly open while breathing to thereby counteract any tendencies to clench the teeth. In addition, breathing should not be forced but should be gentle and easy.

When the device 20 is first used it is recommended that it be used for no more than 4 or 5 minutes at a time. As discomfort decreases a gradual increase of the amount of time the device is used is recommended.

It is suggested that the device 20 be used daily until the user no longer feels pain while using it. Using the device at regular intervals is most effective, with 5 minutes each morning and evening being a preferred routine. The device should never be left in place applying pressure to the occipital area for longer than 30 seconds. Eventually the use of the device will not hurt at all and its use will be pleasant. When tension has been reduced sufficiently one need only use the device when one feels the build up of tension.

Without further elaboration, the foregoing will so fully illustrate my invention that others may, by applying current or future knowledge, readily adapt the same for use under various conditions of service.

What is claimed as the invention is:

1. A device for releasing muscular tension in the head-neck area of a user comprising first pressure applying means projecting in a first direction and having an elongated free edge, the periphery of said edge being arcuate and of a first diameter, second pressure applying means projecting in a direction displaced 120° from said first pressure applying means, said second pressure applying means having an elongated free edge, the periphery of which is arcuate and of a second diameter, said second diameter being smaller than said first diameter, third pressure applying means projecting in a direction displaced 120° from said second pressure applying means and said first pressure applying means, said third pressure applying means having an elongated free edge, the periphery of which is of a third diameter, said third diameter being smaller than said second diameter, each of said pressure applying means including an edge disposed opposite to its free edge being disposed adjacent to one another, said pressure applying means being secured to one another by a pair of end members, said end members being of triangular shape, said device being adapted to be supported in position such that the free edge of either the first, second or third pressure applying means is in contact with the occipital area of the user to apply concentrated pressure to the muscles at said contact area to effect the relaxation of tension from said muscles.

2. The device of claim 1 wherein the triangular end members are each equilateral triangles with the length of their sides being equal to the distance between the free edge of one pressure applying member and the free edge of the immediately adjacent pressure applying member.

3. The device of claim 2 wherein said device is arranged to be disposed upon a surface upon which the user lies, with the free edges of two pressure applying means and with the sides of the end members between the free edges of said pressure applying means disposed on said surface to form a support for said device, whereupon the remaining pressure applying means projects upward with its free edge exposed to support the occipital area of the user as the user lies on said surface to thereby apply muscle-tension relieving pressure to said area.

4. The device of claim 3 wherein the diameter, of said first free edge is at least twice the diameter of said second free edge, which is in turn at least twice the diameter of said third free edge.

5. The device of claim 4 wherein said first diameter is approximately 7/32 inch (5.56 mm), the second diameter is approximately 3/32 inch (2.38 mm) and the third diameter is approximately 1/32 inch (0.79 mm).

* * * * *